United States Patent
Farmer et al.

(10) Patent No.: US 11,377,585 B2
(45) Date of Patent: Jul. 5, 2022

(54) CO-CULTIVATION OF A MYXOBACTERIUM AND ACINETOBACTER FOR ENHANCED PRODUCTION OF EMULSAN

(71) Applicant: LOCUS IP COMPANY, LLC, Solon, OH (US)

(72) Inventors: Sean Farmer, North Miami Beach, FL (US); Ken Alibek, Solon, OH (US); Yajie Chen, Solon, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/905,170

(22) Filed: Jun. 18, 2020

(65) Prior Publication Data

US 2020/0399526 A1    Dec. 24, 2020

Related U.S. Application Data

(60) Provisional application No. 62/864,113, filed on Jun. 20, 2019.

(51) Int. Cl.
| | | |
|---|---|---|
| *C09K 8/582* | (2006.01) | |
| *C12P 21/02* | (2006.01) | |
| *C12N 1/20* | (2006.01) | |
| *C12P 19/04* | (2006.01) | |
| *C12P 7/6463* | (2022.01) | |

(52) U.S. Cl.
CPC .......... *C09K 8/582* (2013.01); *C12N 1/20* (2013.01); *C12P 7/6463* (2013.01); *C12P 19/04* (2013.01); *C12P 21/02* (2013.01)

(58) Field of Classification Search
CPC ......... C12P 21/02; C12P 19/04; C12P 7/6463; C12P 19/26; C12P 39/00; C12N 1/20
See application file for complete search history.

(56) References Cited

U.S. PATENT DOCUMENTS

| | | |
|---|---|---|
| 4,332,904 A | 6/1982 | Kurane et al. |
| 4,395,353 A * | 7/1983 | Gutnick ............ C12N 1/205 516/72 |
| 4,450,908 A | 5/1984 | Hitzman |
| 5,165,477 A | 11/1992 | Shell et al. |
| 7,422,737 B1 | 9/2008 | Nussinovitch et al. |
| 7,681,638 B2 | 3/2010 | Soni et al. |
| 8,316,933 B2 | 11/2012 | Kohr |
| 9,422,470 B2 | 8/2016 | Xu et al. |
| 2002/0143071 A1 | 10/2002 | Gutnick et al. |
| 2008/0107689 A1 | 5/2008 | Seiskari |
| 2009/0029879 A1 | 1/2009 | Soni et al. |
| 2010/0044031 A1 | 2/2010 | Fallon et al. |
| 2010/0145116 A1 | 6/2010 | Van Keulen et al. |
| 2012/0039853 A1 | 2/2012 | Corveleyn et al. |
| 2012/0122740 A1 | 5/2012 | Roldan Carrillo et al. |
| 2012/0258126 A1 | 10/2012 | Scholler et al. |
| 2013/0062053 A1 | 3/2013 | Kohr et al. |
| 2013/0337108 A1 | 12/2013 | Van Hee |
| 2014/0273150 A1 | 9/2014 | Angel |
| 2014/0315765 A1 | 10/2014 | McDaniel |
| 2015/0037302 A1 | 2/2015 | Bralkowski et al. |
| 2015/0044356 A1 | 2/2015 | Bootsma et al. |
| 2015/0305347 A1 | 10/2015 | Wicks et al. |
| 2016/0152525 A1 | 6/2016 | Chelle et al. |
| 2016/0222280 A1 | 8/2016 | Kohr et al. |
| 2017/0107477 A1 | 4/2017 | Farmer et al. |
| 2018/0272396 A1 | 9/2018 | Farmer et al. |
| 2018/0303934 A1 | 10/2018 | Clube et al. |

FOREIGN PATENT DOCUMENTS

| | | |
|---|---|---|
| CN | 102352227 A | 2/2012 |
| CN | 102533597 A | 7/2012 |
| WO | 8103338 A1 | 11/1981 |
| WO | 9525163 A1 | 9/1995 |
| WO | 2010003086 A1 | 1/2010 |
| WO | 2013110132 A1 | 8/2013 |
| WO | 2014152350 A1 | 9/2014 |
| WO | 2017044953 A1 | 3/2017 |
| WO | 2018049182 A2 | 3/2018 |
| WO | 2018129299 A1 | 7/2018 |
| WO | 2019046183 A1 | 3/2019 |
| WO | 2019051380 A1 | 3/2019 |
| WO | 2019089730 A1 | 5/2019 |

OTHER PUBLICATIONS

Bhatia et al. Biotechnological potential of microbial consortia and future perspectives. Critical Reviews in Biotechnology (2018), 38(8): 1209-1229.*

Kunze et al. Stigmatellin, a new antibiotic from Stigmatella aurantiaca (Myxobacteriales), production, physico-chemical and biological properties. The Journal of Antibiotics (1984), vol. XXXVII, No. 5, p. 454-461.*

Hrenovic et al. Immobilisation of Acinetobacter calcoaceticus using natural carriers. Water SA (2005), 31(2): 261-266.*

Bach, H., et al., "An Exocellular Protein from the Oil-Degrading Microbe Acinetobacter venetianus RAG-1 Enhances the Emulsifying Activity of the Polymeric Bioemulsifier Emulsan." Applied and Environmental Microbiology, May 2003, 69(5): 2608-2615.

Bangrak, P., et al., "Continuous Ethanol Production Using Immobilized Yeast Cells Entrapped in Loofa-Reinforced Alginate Carriers." Brazilian Journal of Microbiology, 2011, 42: 676-684.

(Continued)

*Primary Examiner* — Iqbal H Chowdhury
(74) *Attorney, Agent, or Firm* — Saliwanchik, Lloyd & Eisenschenk

(57) ABSTRACT

Methods are provided for enhanced production of one or more microbial biopolymers, the methods comprising co-cultivating *Stigmatella aurantiaca* and *Acinetobacter venetianus*. In certain embodiments, the one or more biopolymers are emulsan. In certain embodiments, other microbial growth by-products are produced, such as biosurfactants. Microbe-based products produced according to the subject methods are also provided, as well as their uses in, for example, oil and gas recovery, agriculture, and health care.

8 Claims, No Drawings

(56) References Cited

OTHER PUBLICATIONS

Bull, C. T., et al., "Interactions Between Myxobacteria, Plant Pathogenic Fungi, and Biocontrol Agents." Plant Disease, Aug. 2002, 86: 889-896.
Chong, H., et al., "Microbial Production of Rhamnolipids: Opportunities, Challenges and Strategies." Microbial Cell Factories, 2017, 16(137): 1-12.
Das, N., et al., "Progress in the Development of Gelling Agents for Improved Culturability of Microorganisms." Frontiers in Microbiology, Jul. 2015, 6(698): 1-7.
De Almeida, D., et al., "Biosurfactants: Promising Molecules for Petroleum Biotechnology Advances." Frontiers in Microbiology, Oct. 2016, 7(1718): 1-14.
De Brito, D., Biosurfactants from renewable raw materials, Universidade do Minho Departamento de Engenharia Biologica, Nov. 2013, pp. 1-93.
Duarte, J. C., et al., "Effect of Immobilized Cells in Calcium Alginate Beads in Alcoholic Fermentation." AMB Express, 2013, 3(31): 1-8.
Ghojavand, H., et al., "Isolation of Thermotolerant, Halotolerant, Facultative Biosurfactant-Producing Bacteria." Applied Microbiology and Biotechnology, 2008, 80: 1073-1085.
Mueller, S., et al., "Bacillaene and Sporulation Protect Bacillus Subtilis from Predation by Myxococcus Xanthus." Sep. 2014, 80(18): 5603-5610.
Mueller, S., et al., "Predation by Myxococcus Xanthus Induces Bacillus Subtilis To Form Spore-Filled Megastructures." Applied and Environmental Microbiology, Jan. 2015, 81(1): 203-210.
Mueller, S., et al., "Identification of Functions Affecting Predator-Prey Interactions between Myxococcus Xanthus and Bacillus Subtilis" Journal of Bacteriology, Dec. 2016, 198(24): 3335-3344.
Mujumdar, S., et al., "Production, Characterization, and Applications of Bioemulsifiers (BE) and Biosurfactants (BS) Produced by *Acinetobacter* spp.: A Review." Journal of Basic Microbiology, 2019, 59: 277-287.
Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.
Perez, J., et al., "Myxococcus Xanthus Induces Actinorhodin Overproduction and Aerial Mycelium Formation by Streptomyces Coelicolor." Microbial Biotechnology, 2011, 4(2): 175-183.
Rocha E Silva, F.C.P., et al., "Yeasts and bacterial biosurfactants as demulsifiers for petroleum derivative in seawater emulsions." AMB Expr., 2007, 7(202): 1-13.
Sen, R., "Biosurfactants: Advances in Experimental Medicine and Biology." Landes Bioscience and Springer Science +Business Media, LLC, 2010, 672: 1-331.
Sharma, A. et al., "A study on biosurfactant production in *Lactobacillus* and *Bacillus* sp." Int. J. Curr. Microbiol. App. Sci., 2014, 3(11): 723-733.

\* cited by examiner

CO-CULTIVATION OF A MYXOBACTERIUM AND ACINETOBACTER FOR ENHANCED PRODUCTION OF EMULSAN

CROSS-REFERENCE TO RELATED APPLICATION

This application claims priority to U.S. Provisional Patent Application No. 62/864,113, filed Jun. 20, 2019, which is incorporated herein by reference in its entirety.

BACKGROUND OF THE INVENTION

Cultivation of microorganisms such as bacteria, yeasts and fungi, is important for the production of a wide variety of useful bio-preparations. Microorganisms play crucial roles in, for example, food industries, pharmaceuticals, agriculture, oil and gas recovery, mining, environmental remediation, and waste management; however, one of the factors restricting commercialization of microbe-based products has been that it is particularly expensive and/or unfeasible to produce these products on a large scale.

Two principle forms of microbe cultivation exist: submerged cultivation and surface cultivation. Bacteria, yeasts and fungi can all be grown using either the surface or submerged cultivation methods. Both cultivation methods require a nutrient medium for the growth of the microorganisms. The nutrient medium, which can either be in a liquid or a solid form, typically includes a carbon source, a nitrogen source, salts and appropriate additional nutrients and microelements. The pH and oxygen levels are maintained at values suitable for a given microorganism.

Microbes have great potential to be beneficial to a wide variety of industries, such as, for example, the oil and gas industry through microbially enhanced oil recovery (MEOR). Oil exists in small pores and narrow fissures within the body of reservoir rocks underneath the surface of the earth. Natural pressure of the reservoir causes the oil to flow up to the surface, thereby providing primary production; however as oil production progresses, the reservoir pressure is depleted to a point at which artificial lift or pumping is required to maintain oil production.

When it is necessary to provide external energy for the reservoir to achieve additional oil recovery (secondary recovery, or enhanced oil recovery (EOR)), the extra energy can be introduced by injecting gas (gas injection) and/or water (water flooding). With water flooding in particular, water is injected into the subterranean oil reservoir for the purpose of displacing the crude oil from the pore spaces of the reservoir rock towards the producing wells.

Primary recovery generally results in an average recovery of only a fraction of the oil originally present in an oil bearing formation. Secondary recovery generally recovers another 10% by the time it becomes uneconomical to continue. It is not unusual, then, for 60 to 70% of the oil originally in the formation to remain, even after secondary recovery reaches is economical limit. In this situation, a third stage of oil recovery/EOR, so-called tertiary production, can be considered.

At this tertiary stage, technically advanced methods are employed to either modify the properties of reservoir fluids or the reservoir rock characteristics. In general, the methods can be classified into four main categories: thermal methods, chemical methods, miscible or solvent injection, and microbial methods.

Microbial enhanced oil recovery (MEOR) in particular is a multidisciplinary field incorporating, among others: geology, chemistry, microbiology, fluid mechanics, petroleum engineering, environmental engineering and chemical engineering. The microbial processes proceeding in MEOR can be classified according to the oil production problem in the field: well bore clean-up removes mud and other debris blocking the channels where oil flows; well stimulation improves the flow of oil from the drainage area into the well bore; and enhanced water floods increase microbial activity by injecting selected microbes and sometimes nutrients.

Thus, MEOR uses microorganisms and/or their metabolites to enhance the recovery of residual oil. Nutrients and suitable bacteria, which preferably grow under the anaerobic reservoir conditions, can be injected into a reservoir. Microbial by-products, which can include biosurfactants, biopolymers, acids, solvents, gases, and enzymes, for example, can modify the properties of the oil and the interactions between oil, water, and the porous media, alter the permeability of subterranean formations, and ultimately increase the mobility and recovery of oil.

Specifically, interest in microbial surfactants has been steadily increasing in recent years due to their diversity, environmentally friendly nature, possibility of large-scale production, selectivity, performance under extreme conditions, and potential applications in environmental protection. Microbially-produced surfactants, i.e., biosurfactants, reduce the interfacial tension between water and oil and, therefore, a lower hydrostatic pressure is required to move the liquid entrapped in the pores to overcome the capillary effect. Secondly, biosurfactants contribute to the formation of micelles providing a physical mechanism to mobilize oil in a moving aqueous phase.

Other microbial by-products have also increased in importance, including certain enzymes, acids, gases and biopolymers.

As oil wells mature, pumping oil at an economically viable rate becomes more difficult and costly. Oil wells that are nearing the end of their economically useful life are called "marginal" or "stripper" wells. These wells often go abandoned prematurely, leaving behind hundreds or even thousands of barrels of valuable crude oil. Accordingly, there is a continuing need to develop improved methods of oil recovery, even from wells that might be considered too mature to be productive. Thud, improved methods of cultivation and mass production of microorganisms and microbial metabolites that could be useful in MEOR could greatly benefit the oil and gas industry.

BRIEF SUMMARY OF THE INVENTION

The subject invention provides methods of producing microorganisms and their growth by-products. More specifically, the subject invention provides for improved methods of producing microbial biopolymers and other useful microbial metabolites. Advantageously, the microbe-based products and methods of the subject invention are environmentally-friendly, operational-friendly and cost-effective.

In preferred embodiments, the subject invention provides methods for producing one or more microbial growth by-products, the methods comprising co-cultivating a myxobacterium and an *Acinetobacter* spp. bacterium in a fermentation system. Advantageously, in certain embodiments, the total cell biomass and/or the total production of the one or more growth by-products achieved when using the subject methods is greater than when pure cultures of the individual microbes are cultivated separately.

In certain preferred embodiments, methods for co-cultivating microorganisms and/or for production of one or more microbial growth by-products are provided, the methods comprising inoculating a fermentation system comprising liquid growth medium with a first microorganism and a second microorganism, wherein the first microorganism is a myxobacterium and the second microorganism is a *Acinetobacter* spp. bacterium.

In one embodiment, the myxobacterium is a *Stigmatella* spp. bacterium and the *Acinetobacter* is, for example, *A. venetianus*. In one embodiment, the *A. venetianus* is strain RAG-1 (ATCC 31012).

The microorganisms can be co-cultivated using cultivation processes ranging from small to large scale. These cultivation processes can include, but are not limited to, submerged cultivation/fermentation, solid state fermentation (SSF), and hybrids, modifications and/or combinations thereof. In some embodiments, the cultivation process is a fed-batch process.

In one embodiment, co-cultivation is carried out using submerged fermentation. In one embodiment a hybrid of SSF and submerged fermentation is used, wherein a particulate anchoring carrier is suspended in the liquid culture medium to serve as a site for cell attachment and/or biofilm formation. This is particularly useful for the growth of myxobacteria, which can exhibit enhanced growth on a solid surface.

The liquid growth medium can comprise sources of, for example, carbon, nitrogen, proteins, vitamins and/or minerals. In certain embodiments, the nutrient medium is customized for production of a high concentration of one or more specific microbial growth by-products. In one embodiment, the liquid nutrient medium comprises a foam preventer, such as, for example, canola oil.

In some embodiments, the particulate anchoring carrier is suspended in the liquid culture medium prior to, concurrently with, or after the liquid culture medium is inoculated with the first and/or second microorganisms.

In one embodiment, the anchoring carrier can be any material suitable for serving as a nucleation site for bacterial attachment and/or growth. In some embodiments, the material comprises a plurality of individual fine particles, e.g., grains, which are about 0.1 μm to about 5 mm in diameter. Bacteria will attach to the particles and accumulate thereon, producing bacterial-carrier masses.

The anchoring carrier can be inert, or it can carry and/or comprise additional nutrients and/or microbial inoculant. In certain embodiments, the anchoring carrier can be porous. The anchoring carrier can comprise synthetic materials and/or naturally-derived materials.

In one embodiment, the anchoring carrier comprises balls made of, for example, glass, a polymer (e.g., polylactic acid (PLA)), agar, or gelatin. The anchoring carrier can be pieces of, for example, a chopped sponge or loofa. In one embodiment, the anchoring carrier can comprise foodstuff, for example, seeds, nuts, beans or even pieces of chopped fruit, such as bananas.

In preferred embodiments, the anchoring carrier comprises fine grains of cellulose and/or corn flour.

Advantageously, the use of the anchoring carrier provides for increased production of bacterial biomass due to, for example, the increased surface area upon which the bacteria can attach and accumulate. Additionally, the accumulation of bacterial biomass can lead to increases in the production of beneficial growth by-products, such as biopolymers and other secondary metabolites.

In one embodiment, bacteria grow in the form of a biofilm on the particulate anchoring carrier. In one embodiment, some bacteria grow in the liquid culture medium and some bacteria grow on the particulate anchoring carrier.

In some embodiments, the cultivation method utilizes fed-batch cultivation. The fermentation reactor can be fed with, for example, an oil-based defoamer, carbon sources (e.g., liquefied paraffin), pH adjusters, and/or other additional nutrient sources as needed. "Feeding" of the fermentation reactor can occur, for example, at 24 hours, at 48 hours, or multiple times, for example, every 24 to 48 hours.

According to the subject methods, the first and second microorganisms can be incubated in the fermentation system for a time period sufficient to achieve a desired effect, e.g., production of a desired amount of cell biomass or a desired amount of one or more microbial growth by-products. In some embodiments, fermentation occurs for 24 hours up to 2 or 3 days or longer, at a temperature of 20 to 30° C.

In preferred embodiments, the methods of the subject invention can be used to produce one or more microbial growth by-products. In certain embodiments, the growth by-products are one or more biopolymers.

In specific embodiments, the methods can be used to produce emulsan, a biopolymer with emulsifying capabilities. In certain embodiments, the methods can be used to produce from 1 to 100 g/L of emulsan.

In some embodiments, the one or more growth by-products can also include other metabolites, for example, enzymes, biosurfactants, acids, solvents, gases, proteins, peptides, amino acids, alcohols, hormones, lipids, carbohydrates, antibiotics, pigments, and other bioactive compounds.

Advantageously, in certain embodiments, the methods of the subject invention can result in the production of biopolymers and/or other growth by-products at greater concentrations than when pure cultures of the individual microbes are cultivated.

In certain embodiments, the subject invention provides microbe-based products produced according to the subject methods, as well as their uses in, for example, improved oil production, bioremediation and mining; waste disposal and treatment; promoting plant health and productivity; and reclaiming and/or restoring the health of soils.

The microbe-based products can comprise the entire culture produced according to the subject methods, including the first and/or the second microorganisms and/or their growth by-products, as well as residual growth medium, particulate anchoring carrier and/or nutrients.

The microorganisms can be live, viable or in an inactive form. They can be in the form of a biofilm, vegetative cells, spores, and/or a combination thereof. In certain embodiments, no microbes are present, wherein the composition comprises microbial growth by-products, e.g., biopolymers, which have been extracted from the culture and, optionally, purified.

DETAILED DESCRIPTION

The subject invention provides methods of producing microorganisms and their growth by-products. Advantageously, the microbe-based products and methods of the subject invention are environmentally-friendly, operational-friendly and cost-effective.

In preferred embodiments, the subject invention provides methods for enhanced production of one or more microbial growth by-products, the methods comprising co-cultivating a myxobacterium and a strain of *Acinetobacter* spp. In a specific embodiment, the growth by-products include a biopolymer, such as, for example, emulsan.

The growth by-products can also include other metabolites, for example, enzymes, biosurfactants, acids, solvents, gases, proteins, peptides, amino acids, alcohols, hormones, lipids, carbohydrates, antibiotics, and other organic and/or bioactive compounds.

Advantageously, the total cell biomass and/or the total production of the one or more growth by-products achieved according to the subject methods can be greater than when pure cultures of the individual microbes are cultivated separately.

Selected Definitions

As used herein, a "biofilm" is a complex aggregate of microorganisms, such as bacteria, wherein the cells adhere to each other and/or to a surface using an extracellular polysaccharide matrix. The cells in biofilms are physiologically distinct from planktonic cells of the same organism, which are single cells that can float or swim in liquid medium.

As used herein, "co-cultivation" means cultivation of more than one microorganism in a single fermentation system. In some instances, the microorganisms interact with one another, either antagonistically or symbiotically, resulting in a desired effect, e.g., a desired amount of cell biomass growth or a desired amount of metabolite production. In one embodiment, this antagonistic or symbiotic relationship can result in an enhanced effect, for example, the desired effect can be magnified when compared to what results from cultivating only one of the chosen microorganisms on its own. In an exemplary embodiment, one microorganism, e.g., a *Stigmatella* sp., can serve as a stimulator for the production of biopolymers or other metabolites by the other microorganism, e.g., an *Acinetobacter* sp.

As used herein, "enhancing" refers to improving and/or increasing.

As used herein, "fermentation" refers to cultivation or growth of cells under controlled conditions. The growth could be aerobic or anaerobic.

As used herein, an "isolated" or "purified" nucleic acid molecule, polynucleotide, polypeptide, protein, organic compound, or other compound is substantially free of other material, such as cellular material, genes or gene sequences, and/or amino acids or amino acid sequences, with which it is associated in nature. A purified or isolated microbial strain is removed from the environment in which it exists in nature and/or in which it was cultivated. Thus, the isolated strain may exist as, for example, a biologically pure culture, or as spores (or other forms of the strain).

In certain embodiments, purified compounds are at least 60% by weight the compound of interest. Preferably, the preparation is at least 75%, more preferably at least 90%, and most preferably at least 99%, by weight the compound of interest. For example, a purified compound is one that is, preferably, at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state or in spore form, or a mixture of both. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells or spores may be absent, or present at, for example, a concentration of at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ or more CFU per milliliter of the composition.

As used herein, a "microbe-based product," is a product to be applied in practice to achieve a desired result. The microbe-based product can be simply a microbe-based composition harvested from the cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "polymer" refers to any macromolecular compound prepared by bonding one or more similar molecular units, called monomers, together. Polymers include synthetic and natural polymers. Exemplary polymers include rubbers, starches, resins, gums (e.g., guar gum, xanthan gum, and welan gum), neoprene, nylon, PVC, silicone, cellulose, polystyrene, polyethylene, polypropylene, polyacrylonitrile, polyamines, polysaccharides (e.g., emulsan), polynucleotides, polybutylene adipate terephthalate (PBAT), polyhydroxyalkanoates (PHAs), polybytlene succinate (PBS), polycaprolactone (PCL), polyglycolic acid (PGA), polyhydroxybutyrates (PHBs), polyesters such as polylactide (PLA), polyacrylamides (PAM), and others.

Further included in the term polymer is the term "biopolymer," "biological polymer" or "renewable polymer," which as used herein, means a natural polymeric substance, or a polymeric substance produced by, or occurring in, a living organism. One characteristic of biopolymers is their ability to biodegrade. Biopolymers can include polynucleotides (e.g., RNA and DNA), polysaccharides (e.g., linearly bonded polymeric carbohydrates), and polypeptides (i.e., polymers of amino acids). Specific examples of biopolymers include, but are not limited to, rubbers, emulsan, suberin, melanin, lignin, cellulose, xanthan gum, guar gum, welan gum, levan, alginate, and many others.

As used herein, "reduces" means a negative alteration of at least 1%, 5%, 10%, 25%, 50%, 75%, or 100%.

As used herein, "surfactant" means a compound that lowers the surface tension (or interfacial tension) between two liquids, between a liquid and a gas, or between a liquid and a solid. A "biosurfactant" is a surface-active substance produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Use of the term "comprising" contemplates other embodiments that "consist" or "consist essentially" of the recited components(s).

Unless specifically stated or obvious from context, as used herein, the term "or" is understood to be inclusive. Unless specifically stated or obvious from context, as used herein, the terms "a," "and," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Methods of Co-Cultivation

The subject invention provides materials and methods for the production of biomass (e.g., viable or inactive cellular material), extracellular metabolites, and/or intracellular components. In preferred embodiments, the subject invention provides improved methods for producing one or more microbial growth by-products, wherein the methods comprise co-cultivating two or more different microorganisms in a fermentation reactor.

Advantageously, the total cell biomass and/or the total production of the one or more growth by-products achieved when using the subject co-cultivation methods can be greater compared to when cultures of the individual microbes are cultivated.

More specifically, in preferred embodiments, the subject invention provides methods for enhanced production of one or more microbial growth by-products, the method comprising co-cultivating a first microorganism and a second microorganism in a submerged fermentation reactor under conditions favorable for growth and production of the one or more growth by-products. In certain embodiments, the first microorganism is a myxobacterium and the second microorganism is a strain of *Acinetobacter* spp.

The microorganisms can be co-cultivated using cultivation systems ranging from small to large scale. These cultivation systems can include, but are not limited to, submerged cultivation/fermentation, solid state fermentation (SSF), and hybrids, modifications and/or combinations thereof.

In certain preferred embodiments, the methods for co-cultivating microorganisms and/or for producing microbial growth by-products comprise: inoculating a fermentation system comprising a liquid nutrient medium with a first microorganism and inoculating the fermentation system with a second microorganism, wherein the first microorganism is a *Stigmatella* spp. bacterium and the second microorganism is a strain of *Acinetobacter* spp. Even more preferably, in one embodiment, the *Stigmatella* is *S. auran-tiaca* and the *Acinetobacter* is a strain of *A. venetianus*. In one embodiment, the strain of *A. venetianus* is "RAG-1" (ATCC 31012).

In certain embodiments, the co-cultivation method utilizes submerged fermentation. In certain embodiments, a hybrid of solid state and submerged fermentation is used, wherein a particulate anchoring carrier is suspended in the liquid culture medium to serve as a site for cell attachment and/or biofilm formation. This is particularly useful for the growth of myxobacteria, which can exhibit enhanced growth on a solid surface or other carrier.

The microbe growth vessel used according to the subject invention can be any fermenter or cultivation reactor for industrial use. In one embodiment, the vessel may have functional controls/sensors or may be connected to functional controls/sensors to measure important factors in the co-cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, samples may be taken at any point throughout fermentation in order to perform, e.g., CFU count and/or purity measurements. In one embodiment, sampling is performed at the start of fermentation, and multiple times per day (e.g., twice per day) throughout fermentation.

In some embodiments, the cultivation method utilizes fed-batch cultivation. The fermentation reactor can be fed with, for example, an oil-based defoamer, carbon sources (e.g., liquefied paraffin), pH adjusters, and/or other additional nutrient sources as needed.

In one embodiment, the fermentation reactor is connected to a feed container. The feed container preferably holds liquid nutrient medium and/or the other substances for feeding (e.g., transferring or supplementing), into the fermentation reactor. "Feeding" of the fermentation reactor can occur either continuously or at designated time points throughout cultivation.

In certain embodiments, the designated feed time points are at 12 hours, 24 hours, 36 hours, 48 hours or 52 hours after the start of cultivation. In certain embodiments, there are multiple time points at which the nutrient medium and/or other feed substances are fed into the reactor, for example, every 6 hours, every 12 hours, every 24 hours, every 36 hours, or every 48 hours throughout cultivation.

In one embodiment, the fermentation reactor is connected to a foam collection container. Despite the use of a defoamer solution in the nutrient medium and/or feed, some amounts of foam are still naturally produced by the fermentation process. In some embodiments, foam is automatically and/or manually extracted from the reactor and collected in the foam collection container. In some embodiments, the collected foam comprises microbial growth by-products, such as biosurfactants, that can be extracted and, optionally, purified.

In one embodiment, the liquid nutrient medium comprises a carbon source. The carbon source can be a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; hydrocarbons, fats and/or oils, such as soybean oil, rice bran oil, olive oil, corn oil, sesame oil, canola oil, linseed oil and/or paraffins; powdered molasses, etc. These carbon sources may be used independently or in a combination of two or more.

In one embodiment, the liquid nutrient medium comprises a nitrogen source. The nitrogen source can be, for example, potassium nitrate, ammonium nitrate, ammonium sulfate, ammonium phosphate, ammonia, urea, and/or ammonium chloride. These nitrogen sources may be used independently or in a combination of two or more.

In one embodiment, one or more inorganic salts may also be included in the liquid nutrient medium. Inorganic salts can include, for example, potassium dihydrogen phosphate, monopotassium phosphate, dipotassium hydrogen phosphate, disodium hydrogen phosphate, potassium chloride, magnesium sulfate, magnesium chloride, iron (ferrous) sulfate, iron chloride, manganese sulfate, manganese chloride, zinc sulfate, lead chloride, copper sulfate, calcium chloride, calcium carbonate, calcium nitrate, magnesium sulfate, sodium phosphate, sodium chloride, and/or sodium carbonate. These inorganic salts may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, proteins and microelements can be included, for example, peptone, yeast extract, potato extract, beef extract, soybean extract, banana peel extract, and the like, or in purified forms. Amino acids such as, for example, those useful for biosynthesis of proteins, can also be included.

In some embodiments, the particulate anchoring carrier is suspended in the liquid culture medium prior to, concurrently with, or after the liquid culture medium is inoculated with the first and/or second microorganisms.

The particulate anchoring carrier can be any material suitable for serving as a nucleation site for bacterial attachment and growth. In some embodiments, the material comprises a plurality of individual pieces, particles, and/or grains, which are about 0.1 μm to about: 5 mm, 4 mm, 3 mm, 2 mm, 1 mm or 0.5 mm in diameter. Bacteria will attach to the pieces and accumulate thereon, producing bacterial-carrier masses.

The anchoring carrier can be inert, or it can carry and/or comprise additional nutrients and/or microbial inoculant. In certain embodiments, the anchoring carrier can be porous. The anchoring carrier can comprise synthetic materials and/or naturally-derived materials.

In one embodiment, the anchoring carrier comprises sodium alginate beads. The beads can be prepared by, for example, continuously adding a solution comprising 1 to 5%, or 2 to 3% aseptic sodium alginate and, optionally, nutrients and/or bacterial inoculant, into a sterile 1 to 7%, or 2 to 5% calcium chloride solution to form beads.

In one embodiment, the anchoring carrier can comprise balls made of, for example, glass, a polymer (e.g., polylactic acid (PLA)), agar, or gelatin. In one embodiment, the anchoring carrier can be pieces of, for example, a chopped sponge or loofa. In one embodiment, the anchoring carrier can comprise foodstuff, for example, seeds, nuts, beans or even pieces of chopped fruit, such as bananas.

In preferred embodiments, the anchoring carrier comprises fine grains of cellulose and/or corn flour. In one embodiment, the use of fine grains is preferred over larger particles (e.g., greater than 5 mm), because it facilitates scaling-up of the process.

Advantageously, the use of the anchoring carrier provides for increased production of bacterial biomass due to, for example, the increased surface area to which the bacteria can attach and accumulate. Additionally, the accumulation of bacterial biomass can lead to increases in the production of beneficial growth by-products, such as biosurfactants.

In one embodiment, bacteria grow in the form of a biofilm on the anchoring carrier. In one embodiment, some bacteria grow in the liquid culture medium in planktonic form, and some bacteria grow on the anchoring carrier.

In some embodiments, the liquid culture medium is inoculated with the microorganisms prior to, or concurrently with, suspension of the anchoring carrier. In some embodiments, the anchoring carrier is pre-inoculated with the first and/or second microorganism before being suspended in the liquid culture medium.

The method of co-cultivation can further provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid. In certain embodiments, dissolved oxygen (DO) levels are maintained at about 25% to about 75%, about 30% to about 70%, about 35% to about 65%, about 40% to about 60%, or about 50% of air saturation. Air flow can be supplied at, for example, about 0.5 to about 2.0 v/m, or about 1.0 to about 1.5 vvm.

In some embodiments, the method for co-cultivation may further comprise adding acids and/or antimicrobials in the liquid medium before and/or during the co-cultivation process to protect the culture against contamination.

In one embodiment, prior to inoculation, the components of the liquid culture medium can be sterilized. If used, the anchoring carrier is also preferably sterilized, for example, using an autoclave or other method known in the art. Additionally, water used for preparing the medium can be filtered to prevent contamination.

In one embodiment, sterilization of the liquid nutrient medium can be achieved by placing the components of the liquid culture medium in water at a temperature of about 85-100° C. In one embodiment, sterilization can be achieved by dissolving the components in 1 to 3% hydrogen peroxide in a ratio of 1:3 (w/v).

In one embodiment, the equipment used for co-cultivation is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of pH and/or low water activity may be exploited to control unwanted microbial growth.

The pH of the mixture should be suitable for the microorganism(s) of interest. In some embodiments, the pH is about 2.0 to about 11.0, about 3.0 to about 10.0, about 4.0 to about 9.0, about 5.0 to about 8.0, or about 6.0 to about 7.0. In one embodiment, the pH is about 6.6 to 6.9. Buffers, and pH regulators may be used to stabilize pH near a preferred value. In certain embodiments, a basic solution (e.g., 15 to 25%, or 20% NaOH solution) and/or an acid solution (e.g., 15 to 25%, or 20% citric acid) is/are included in the liquid nutrient medium or fed into the reactor during cultivation to automatically maintain and/or adjust pH of the culture. When metal ions are present in high concentrations, use of a chelating agent in the liquid medium may be necessary.

In one embodiment, the method for co-cultivation of microorganisms is carried out at about 5° to about 100° C., about 15° to about 60° C., about 20° to about 45° C., or about 24° to about 30° C. In one embodiment, the co-cultivation may be carried out continuously at a constant temperature. In another embodiment, the co-cultivation may be subject to changing temperatures.

According to the subject methods, the first and second microorganisms can be incubated in the fermentation system for a time period sufficient to achieve a desired effect, e.g., production of a desired amount of cell biomass or a desired amount of one or more microbial growth by-products. The biomass content may be, for example from 5 g/l to 180 g/l or more, or from 10 g/l to 150 g/1.

In some embodiments, fermentation occurs for 24 hours to 1 week, about 2 to 5 days, or about 2 to 3 days. The microbial growth by-product(s) produced by the microorganisms may be retained in the microorganisms or secreted into the growth medium. In certain embodiments, the growth by-product is produced in the form of a foam layer at the top of the culture.

In another embodiment, the method for producing microbial growth by-products may further comprise steps of extracting, concentrating and/or purifying the microbial growth by-product of interest. Alternatively, the microbial growth by-products can be utilized in their crude form, meaning no purification is performed. In a further embodiment, the growth medium may contain compounds that stabilize the activity of the microbial growth by-product.

The methods can be performed in a batch, quasi-continuous, continuous process, or a fed-batch process.

In one embodiment, all of the foam, nutrient medium, cells and/or bacterial-carrier masses are removed upon the completion of the co-cultivation (e.g., upon, for example, achieving a desired cell density, or amount of metabolite). The remaining cell mass can be recycled and/or hydrolyzed to obtain any leftover compounds present in the cells. In this batch procedure, an entirely new batch is initiated upon harvesting of the first batch.

In one embodiment, the process is a fed-batch process, where certain nutrient sources and/or other substances are fed into the reactor at certain time points to replenish the nutrient medium and/or to increase the efficiency of the process. The entire batch is harvested at the end of the cultivation cycle, and an entirely new batch is initiated upon harvesting of the first batch.

In one embodiment, the process is continuous or quasi-continuous, where the growth by-products of interest are collected from the culture, for example, from the foam that forms during co-cultivation and/or from the liquid nutrient medium. In preferred embodiments, the foam and/or medium is placed into a collection container with an optional pH meter. Biomass and/or inoculated anchoring carriers with viable cells remain in the fermentation reactor as an inoculant and the nutrient medium is replenished, e.g., from a feed tank housing fresh nutrient medium, to continue microbial growth and production of metabolites.

In one embodiment, the foam can be extracted on a consistent basis, meaning, for example, every 1 to 24 hours, every other day, or every 2 to 7 days. In another embodiment, the foam can be extracted upon reaching a certain volume. The composition that is removed can be a cell-free foam or broth, and/or it can contain some cells.

Foam and/or broth that are collected from the cultivation system can be processed by washing and/or centrifuging to extract the microbial growth by-products. Optionally, the growth by-products can then be stored, purified, and/or used directly in crude form.

In one embodiment, some or all of the anchoring carriers, if used, can be harvested from the culture and washed using a solvent, for example, low concentration (e.g., 1 to 2%) ethanol. The resulting liquid is then centrifuged to separate growth by-products and cell mass.

Advantageously, the total cell biomass and/or the total production of the one or more growth by-products achieved when using the subject co-cultivation methods can be greater compared to when pure cultures of the individual microbes are cultivated on their own.

In certain embodiments, the total cell biomass achieved according to the subject methods is at least 0.01%, 1%, 5%, 10%, 20%, 30%, 40%, 50%, 60%, 70%, 80%, 90%, 100%, or more, greater than when the first and second microorganisms are cultivated individually.

In certain embodiments, the total concentration of a growth by-product produced according to the subject methods is at least 0.01%, 1%, 5%, 10%, 20%, 30%, 40%, 50%, 60%, 70%, 80%, 90%, 100%, or more, greater than when the first and second microorganisms are cultivated individually.

Microorganisms

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganisms are bacteria, including Gram-positive and Gram-negative bacteria. In specific embodiments, the first microorganism is selected from myxobacteria. Myxobacteria are slime-forming, predatory bacteria that live in groups, or swarms. These swarms may form complex biofilms, as well as fruiting body structures, which are either simple or branched aggregates containing myxospores. During predation, the bacteria secrete predatory molecules, including enzymes, antibiotics and other secondary metabolites, which can include, for example, biosurfactants.

Myxobacteria include, for example, *Myxococcus* spp. (e.g., *M. xanthus, M. fulvus, M. flavescens, M. macrosporus, M. stipitatus, M. virescens, M. coralloides*, and *M. disciformis*), *Stigmatella* spp., *Sorangium cellulosum, Minicystis rosea*, and *Chondromyces crocatus*.

In preferred embodiments, the myxobacterium is a *Stigmatella* sp. selected from, for example, *S. aurantiaca, S. erecta* and *S. hybrid*. Even more preferably, *S. aurantiaca* is used.

In certain embodiments, the second microorganism is selected from *Acinetobacter* spp. bacteria. Members of this Gram-negative, aerobic, non-fermenting genus can be isolated from a broad range of different habitats, including water, soil and living organisms and, despite having been described as non-motile, possess different forms of motility (e.g., twitching).

Preferably, the species of *Acinetobacter* is *A. venetianus*. In certain embodiments, a strain of *Acinetobacter venetianus* known as "RAG-1" (ATCC 31012) is used. *A. venetianus* strains are a useful tool in oil recovery and bioremediation, as they have developed diverse strategies of degrading n-alkanes, such as those found in crude oil. RAG-1, in particular, can produce, for example, emulsan and esterases for such a purpose.

In preferred embodiments, *S. aurantiaca* and a strain of *A. venetianus* are co-cultivated according to the subject methods. Advantageously, in some embodiments, the cell biomass from co-cultivation of these two strains is greater than when pure cultures of the individual microbes are cultivated. Furthermore, in some embodiments, production of biopolymers and/or other metabolites in co-culture is greater than when pure cultures of the individual microbes are used.

In certain embodiments, this enhanced production of growth by-products and/or metabolites is caused by the co-cultivation, wherein the presence of a competitor microorganism induces enhanced production of, for example, defensive molecules and/or self-growth promoters. In certain embodiments, these are biopolymers and/or biosurfactants.

Microbial Growth by-Products

The methods and systems of the subject invention can be used to produce compositions comprising one or more useful microbial growth by-products such as, for example, biopolymers and/or other microbial metabolites.

In preferred embodiment, the growth by-products are one or more biopolymers. For example, in one embodiment, the methods are useful for the production of the powerful emulsifying compound, emulsan. Emulsan is an amphipathic polysaccharide bioemulsifier that interfaces between cell membranes and oil, thus facilitating the process of n-alkanes uptake into the cell. It can also be used to reduce the surface and interfacial tension within an oil well, as well as to make transporting oil through pipelines easier through emulsification of crude oil and lowering viscosity of crude oil. Emulsan is also thought to be useful in other industries, for example, health care, where it might have potential for use as an adjuvant for vaccine delivery.

In certain embodiments, the methods can be used to produce from about 0.1 to about 100 g/L, about 1 to about 50 g/L, or about 5 to about 25 g/L of emulsan.

In some embodiments, the microbial growth by-products can also include one or more biosurfactants. Biosurfactants according to the subject invention can include, for example, glycolipids (e.g., sophorolipids, mannosylerythritol lipids, trehalose lipids, rhamnolipids, and cellobiose lipids), lipopeptides (e.g., surfactins, iturins, fengycins, lichenysins, plipastatins, viscosin, arthrofactin and kurstakins), flavolipids, phospholipids, fatty acid esters, fatty acid ethers, lipoproteins, lipopolysaccharide-protein complexes, and/or polysaccharide-protein-fatty acid complexes.

In certain embodiments, the methods can be used to produce about 0.1 to about 30 g/L about 1 to about 25 g/L, or about 5 to about 25 g/L of the one or more biosurfactants.

In some embodiments, the microbial growth by-products include other metabolites. As used herein, a "metabolite" refers to any substance produced by metabolism (e.g., a growth by-product), or a substance necessary for taking part in a particular metabolic process, for example, enzymes, enzyme inhibitors, biopolymers, acids, solvents, gases, proteins, peptides, amino acids, alcohols, pigments, pheromones, hormones, lipids, ectotoxins, endotoxins, exotoxins, carbohydrates, antibiotics, anti-fungals, anti-virals and/or other organic and/or bioactive compounds. The metabolite content produced by the method can be, for example, at least 0.1%, 1%, 5%, 10%, 20%, 30%, 40%, 50%, 60%, 70%, 80%, or 90%.

In certain embodiments, the one or more growth by-products include enzymes such as, for example, oxidoreductases, transferases, hydrolases, lyases, isomerases and/or ligases. Specific types and/or subclasses of enzymes according to the subject invention can also include, but are not limited to, nitrogenases, proteases, amylases, glycosidases, cellulases, glucosidases, glucanases, galactosidases, moannosidases, sucrases, dextranases, hydrolases, methyltransferases, phosphorylases, dehydrogenases (e.g., glucose dehydrogenase, alcohol dehydrogenase), oxygenases (e.g., alkane oxygenases, methane monooxygenases, dioxygenases), hydroxylases (e.g., alkane hydroxylase), esterases, lipases, ligninases, mannanases, oxidases, laccases, tyrosinases, cytochrome P450 enzymes, peroxidases (e.g., chloroperoxidase and other haloperoxidases), and lactases.

In certain embodiments, the one or more growth by-products include antibiotic compounds, such as, for example, aminoglycosides, amylocyclicin, bacitracin, bacillaene, bacilysin, bacilysocin, corallopyronin A, difficidin, etnangien gramicidin, β-lactams, licheniformin, macrolactinsublancin, oxydifficidin, plantazolicin, ripostatin, spectinomycin, subtilin, tyrocidine, and/or zwittermicin A. In some embodiments, an antibiotic can also be a type of biosurfactant.

In certain embodiments, the one or more growth by-products include anti-fungal compounds, such as, for example, fengycin, surfactin, haliangicin, mycobacillin, mycosubtilin, and/or bacillomycin. In some embodiments, an anti-fungal can also be a type of biosurfactant.

In certain embodiments, the one or more growth by-products include other bioactive compounds, such as, for example, butanol, ethanol, acetate, ethyl acetate, lactate, acetoin, benzoic acid, 2,3-butanediol, beta-glucan, indole-3-acetic acid (IAA), lovastatin, aurachin, kanosamine, reseoflavin, terpentecin, pentalenolactone, thuringiensin (β-exotoxin), polyketides (PKs), terpenes, terpenoids, phenyl-propanoids, alkaloids, siderophores, as well as ribosomally and non-ribosomally synthesized peptides, to name a few.

Microbe-Based Products

The subject invention provides microbe-based products, as well as their use in a variety of applications, including, for example, agriculture, enhanced oil recovery, bioremediation, pharmaceuticals, and cosmetics.

One microbe-based product of the subject invention is simply the fermentation medium containing the microorganisms, microbial growth by-products produced by the microorganisms, any residual nutrients and/or residual particulate anchoring carrier. The microbe-based product may be used with or without extraction and/or purification.

The microorganisms may be in an active or inactive form, or in the form of vegetative cells, biofilm, spores, or a combination thereof. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

In one embodiment, the first and second microorganisms are separated from each other after co-cultivation. In one embodiment, the product comprises a blend of the first and second microorganisms and/or their growth by-products.

In one embodiment, the composition does not comprise live microorganisms. In one embodiment, the composition does not comprise microorganisms at all, whether live or inactive.

In one embodiment, the composition comprises the one or more microbial growth by-products separated from the microorganism that produced them. The growth by-products can be in a purified or unpurified form.

The microorganisms, nutrient medium and/or foam resulting from the microbial growth can be removed from the fermenter and/or collection container and transferred via, for example, piping for immediate use.

In other embodiments, the composition (microbes, foam and/or broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100%, 10% to 90%, 20% to 80%, or 30% to 70%, inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, the product is stored at or below a temperature such as, for example, 20° C., 15° C., 10° C., 5° C. or 4° C., or less. If cells are present and in spore form, the product is, in one embodiment, stored and transported at a low temperature, not higher than 15° C., in order to prevent premature germination.

Methods of Use

The compositions of the subject invention can be used for a variety of purposes. In one embodiment, the composition can be used in agriculture. For example, methods are provided wherein a composition produced according to the subject invention is applied to a plant and/or its environment to treat and/or prevent the spread of pests and/or diseases. The composition can also be useful for enhancing water dispersal and absorption in the soil, as well as enhance nutrient absorption from the soil through plant roots, facilitate plant health, increase yields, and manage soil aeration.

In one embodiment, the subject compositions can be highly advantageous in the context of the oil and gas industry. When applied to an oil well, wellbore, subterranean formation, or to equipment used for recovery oil and/or gas, the compositions produced according to the subject invention can be used in methods for enhancement of crude oil recovery; reduction of oil viscosity; removal and dispersal of paraffin from rods, tubing, liners, and pumps; prevention of equipment corrosion; recovery of oil from oil sands and stripper wells; enhancement of fracking operations as fracturing fluids; reduction of $H_2S$ concentration in formations and crude oil; and cleaning of tanks, flowlines and pipelines.

In one embodiment, the compositions produced according to the subject invention can be used to improve one or more properties of oil. For example, methods are provided wherein the composition is applied to oil or to an oil-bearing formation in order to reduce the viscosity of the oil, convert the oil from sour to sweet oil, and/or to upgrade the oil from heavy crude into lighter fractions.

In one embodiment, the compositions produced according to the subject invention can be used to clean industrial equipment. For example, methods are provided wherein a composition is applied to oil production equipment such as an oil well rod, tubing and/or casing, to remove heavy hydrocarbons, paraffins, asphaltenes, scales and other contaminants from the equipment. The composition can also be applied to equipment used in other industries, for example, food processing and preparation, agriculture, paper milling, and others where fats, oils and greases build up and contaminate and/or foul the equipment.

In one embodiment, the compositions produced according to the subject invention can be used to enhance animal health. For example, methods are provided wherein the composition can be applied to animal feed or water, or mixed with the feed or water, and used to prevent the spread of disease in livestock and aquaculture operations, reduce the need for antibiotic use in large quantities, as well as to provide supplemental proteins and other nutrients.

In one embodiment, the compositions produced according to the subject invention can be used to prevent spoilage of food, prolong the consumable life of food, and/or to prevent food-borne illnesses. For example, methods are provided wherein the composition is applied to a food product, such as fresh produce, baked goods, meats, and post-harvest grains, to prevent undesirable microbial growth.

Other uses for the subject compositions include, but are not limited to, biofertilizers, biopesticides, bioleaching, bioremediation of soil and water, pharmaceutical adjuvants (for increasing bioavailability of orally ingested drugs), cosmetic products, control of unwanted microbial growth, and many others.

Local Production of Microbe-Based Products

In preferred embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities can be located at the location where the microbe-based product will be used. For example, the microbe growth facility may be less than 300, 250, 200, 150, 100, 75, 50, 25, 15, 10, 5, 3, or 1 mile from the location of use.

The microbe growth facilities of the subject invention produces fresh, microbe-based compositions, comprising the microbes themselves, microbial metabolites, and/or other components of the broth in which the microbes are grown. If desired, the compositions can have a high density of vegetative cells or propagules, or a mixture of vegetative cells and propagules.

Because the microbe-based product is generated locally, without resort to the microorganism stabilization, preservation, storage and transportation processes of conventional microbial production, a much higher density of bacteria cells and/or propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, and smaller supplies of starter material, nutrients, pH control agents), which makes the system efficient. Local generation of the microbe-based product also facilitates the inclusion of the growth broth in the product. The broth can contain agents produced during the fermentation that are particularly well-suited for local use.

Advantageously, the compositions can be tailored for use at a specified location. The microbe growth facilities provide manufacturing versatility by the ability to tailor the microbe-based products to improve synergies with destination geographies and harness the power of naturally-occurring local microorganisms and their metabolic by-products to improve oil production. Local microbes can be identified based on, for example, salt tolerance and ability to grow at high temperatures.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Co-Cultivation of *S. aurantiaca* and *A. venetianus* for Production of Emulsan

*A. venetianus* is grown in a small-scale reactor for at least 48 hours to produce a 3.0% inoculum. *S. aurantiaca* is grown in a small-scale reactor for at least 4 days to produce a 1.0% inoculum. The *S. aurantiaca* inoculum can be sampled and tested using slide streaking after 3 days to test for purity.

A fermentation reactor is inoculated with the two inocula. The nutrient medium comprises:

| | |
|---|---|
| Sucrose | 0.5 g/L to 2 g/L |
| Casein hydrolysate | 5 to 15 g/L |
| $MgSO_4 \cdot 7H_2O$ | 0.1 to 1.0 g/L |
| $K_2HPO_4$ | 0.01 to 0.5 g/L |
| $KH_2PO_4$ | 0.01 to 0.5 g/L |
| $CaCl_2$ | 0.01 to 0.5 g/L |
| $(NH_4)_2SO_4$ | 1 to 5 g/L |
| Trace elements | 0.5 to 3 g/L |
| DI Water | Remaining volume to 1 L |

Additionally, the nutrient medium includes fine grain particulate anchoring carrier comprising cellulose (1.0 to 5.0 g/L) and/or corn flour (1.0 to 5.0 g/L).

An aqueous base solution comprising 20% NaOH and/or an aqueous acid solution comprising 20% citric acid are fed into the reactor to adjust and maintain pH automatically to/at about 6.6 to 7.0, or about 6.8. Then, an oil-based defoamer (10 to 30 ml/L), such as, e.g., DG-959 (Organic Defoamer Group), and/or canola oil, is added to reduce foam production in the reactor. Additional defoamer can be fed throughout fermentation as needed to reduce foam production.

Cultivation is carried out for about 2 to 3 days. Temperature is maintained at about 24° C.; DO is maintained at about 50%; and air flow rate is maintained at about 1 vvm.

Throughout cultivation the reactor is fed with canola oil (6%, once every 24 hours) and clear liquid paraffin (7%, after 24 hours).

Temperature is maintained at about 24° C.; DO is maintained at about 50%; and air flow rate is maintained at about 1 vvm. Sampling of the fermenter and the foam collection tank for CFU count and/or purity is performed at 0 hr., then twice per day throughout fermentation. Sampling can also occur at the time that harvesting of the culture occurs, i.e., after 5 days of cultivation.

After the fermentation cycle is finished, the culture is harvested from the reactor. A foam layer comprising microbial growth by-products can also be produced during fermentation. This foam layer is extracted and collected in a collection container.

The harvested culture, as well as the extracted foam, can be processed to purify emulsan using, for example, ethyl acetate extraction and/or rotary evaporation purification.

REFERENCES

Su, W T., et al. (2009). "Optimizing emulsan production of *A. venetianus* RAG-1 using response surface methodology." Appl. Microbiol. Biotech. 84:2, 271-279.

The invention claimed is:
1. A method for enhanced production of one or more microbial growth by-products selected from the group consisting of biopolymers and biosurfactants, the method comprising co-cultivating a first microorganism and a second microorganism in a fermentation reactor comprising a liquid nutrient medium and incubating the microorganisms in the reactor under conditions favorable for growth and production of the one or more microbial growth by-products, feeding clear liquefied paraffin into the reactor after 24 hours of incubation, extracting the one or more growth by-products from the reactor, and, optionally, purifying the one or more growth by-products, wherein the first microorganism is *Stigmatella aurantiaca* and the second microorganism is *Acinetobacter venetianus* RAG-1, wherein the biopolymer is emulsan and the biosurfactant is a glycolipid or a lipopeptide, and wherein a greater concentration of the one or more microbial growth by-products is achieved than would be achieved if the first and second microorganisms were cultivated individually.

2. The method of claim 1, wherein the liquid nutrient medium comprises sucrose, casein hydrolysate, magnesium sulfate, dipotassium phosphate, monopotassium phosphate, calcium chloride, ammonium sulfate, trace metals, and water.

3. The method of claim 1, further comprising suspending a particulate anchoring carrier in the liquid nutrient medium.

4. The method of claim 3, wherein the first and/or second microorganism attaches to the particulate anchoring carrier and accumulates thereon in the form of a biofilm to form a plurality of bacterial-carrier masses.

5. The method of claim 1, further comprising adding an aqueous base solution comprising 15 to 25% NaOH and/or an aqueous acid solution comprising 15 to 25% citric acid to the reactor.

6. The method of claim 1, comprising feeding 7% of clear liquefied paraffin into the reactor after 24 hours of incubation.

7. The method of claim 1, further comprising feeding 6% oil-based defoamer into the reactor every 24 hours.

8. The method of claim 1, wherein the first microorganism stimulates enhanced production of the one or more growth by-products by the second microorganism.

* * * * *